United States Patent [19]

Vincent et al.

[11] Patent Number: 5,151,432

[45] Date of Patent: Sep. 29, 1992

[54] SUBSTITUTED AMINO ACID COMPOUNDS

[75] Inventors: Michel Vincent, Bagneux; Georges Remond, Versailles; Bernard Portevin, Elancourt; Yolande Herve, Puteaux; Jean Lepagnol, Chatou, all of France

[73] Assignee: Adir et Compagnie, Courbevoie, France

[21] Appl. No.: 629,823

[22] Filed: Dec. 19, 1990

[30] Foreign Application Priority Data

Dec. 20, 1989 [FR] France ................ 89 16881

[51] Int. Cl.$^5$ .................... C07D 453/06; A61K 37/02
[52] U.S. Cl. .................... 514/299; 546/112
[58] Field of Search ................ 546/112; 514/299

[56] References Cited

FOREIGN PATENT DOCUMENTS 0288907 11/1988 European Pat. Off. .

OTHER PUBLICATIONS

Chem. Ber. 103, 788–789 (1970), König und Geiger.
Organic Preparations and Procedures Int. 15(1-2), 35–40 (1983), Kaltenbronn, DeJohn, and Krolls.
Biochem. J. (1977) 167, 501–504, Ryan et al., "A Simple Radioassay for Angiotensin–Converting Enzyme"..
Chemical Abstracts Service: 109: 38242, 1987.
Chemical Abstracts Service: 104: 51091d, 1985.
Chemical Abstracts Service: 100: 210436, 1984.

*Primary Examiner*—C. Warren Ivy
*Assistant Examiner*—Catherine S. K. Scalzo
*Attorney, Agent, or Firm*—Gordon W. Hueschen

[57] ABSTRACT

The invention relates to the compounds of formula (I):

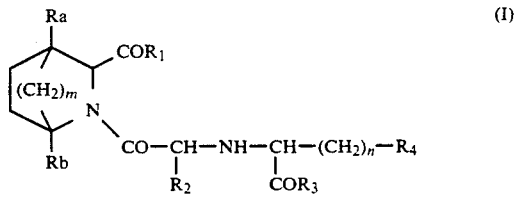

in which:

$R_1$ represents a linear or branched, lower or higher alkoxy group or a substituted or unsubstituted amino group, $R_2$ represents a lower alkyl group unsubstituted or substituted with an amino group, $R_3$ represents an amino, lower or higher alkoxy or a hydroxyl group, with the proviso, however, that at least one amino group is present in $R_1$ or $R_3$, $R_4$ represents a hydrogen atom or an aryl group, m is equal to 1 or 2, n is between 1 and 6, and Ra and Rb, which may be identical or different, represent a hydrogen atom when m=1, or a hydrogen atom or an alkyl group when m=2 and medicinal products.

7 Claims, No Drawings

SUBSTITUTED AMINO ACID COMPOUNDS

The present invention relates to new substituted amino acid compounds.

Among known converting enzyme inhibitors, some have also been described as being nootropic agents. This is the case with compounds mentioned in European Patent Applications EP 307,872, EP 288,907 and EP 243,645, which possess properties as modulators of cognitive dysfunctions.

The compounds of the present invention, apart from the fact that they are new, are distinct from the nootropics of the prior art by the intensity of their pharmacological effects.

Indeed, they exert a facilitatory activity with respect to the memory processes at minimal doses much lower than those of the most active nootropic taken as a reference, oxiracetam.

This memory enhancing effect is exerted, in particular, via cholinergic neurotransmission. In addition, the compounds of the invention possess an inhibitory effect on the angiotensin enzyme converting, which endows them with an antihypertensive effect and a preventive effect of the consequences of hypertension, one of the most important risk factors in cerebral pathology (stroke, multi-infarct dementia).

Thus, these different properties imply that the compounds of the invention appear to be much more suitable for use in therapy than those of related structure described in the literature.

The invention relates more especially to new bicyclic amino acid compounds corresponding to the general formula (I):

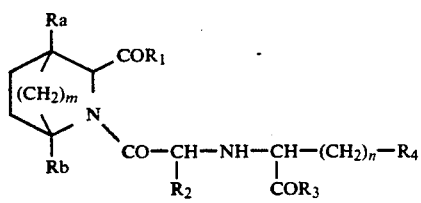

in which:
$R_1$ represents a linear or branched, lower or higher alkoxy group or an amino group optionally substituted with one or two linear or branched lower alkyl groups,
$R_2$ represents a linear or branched lower alkyl group optionally substituted with an amino group,
$R_3$ represents an amino group, a linear or branched, lower or higher alkoxy group or a hydroxyl group, with the proviso, however, that at least one amino group is present in $R_1$ or $R_3$,
$R_4$ represents a hydrogen atom or an aryl group,
m is equal to 1 or 2,
n is between 1 and 6, and
Ra and Rb, which may be identical or different, represent a hydrogen atom when m=1, or a linear or branched lower alkyl group or a hydrogen atom when m=2,
the term lower indicating that the groups so described comprise from 1 to 6 carbon atoms the term higher indicating that the groups so described comprise from 7 to 12 carbon atoms, their enantiomers, diastereoisomers and epimers as well as their addition salts with a pharmaceutically acceptable acid or base.

Among pharmaceutically acceptable acids, hydrochloric, sulfuric, tartaric, maleic, fumaric, oxalic, methanesulfonic and camphoric acids, and the like, may be mentioned without implied limitation.

Among pharmaceutically acceptable bases, sodium hydroxide, potassium hydroxide, tert-butylamine, and the like, may be mentioned without implied limitation.

The invention also encompasses the process for preparing the compounds of formula (I), wherein the compound of formula (II):

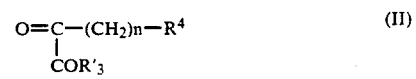

in which $R_4$ has the same meaning as in the formula (I) and $R'_3$ represents an amino or linear or branched, lower or higher alkoxy group, is subjected to a reductive amination in the presence of an alkali metal mixed hydride such as sodium cyanoborohydride with an amino acid of formula (III) in which the acid function is protected:

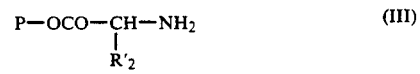

in which P is an alkyl group such as tert-butyl and $R'_2$ a linear or branched lower alkyl group optionally substituted with an amino group which is itself protected with a protective group such as benzyloxycarbonyl, to obtain a compound of formula (IV):

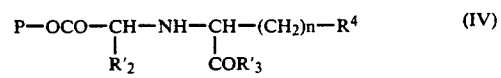

in which $R'_2$, $R'_3$, $R_4$, P and n have the same meanings as above, the isomers of which are optionally separated by a conventional separation technique and which is deprotected in an acid medium to obtain a compound of formula (V):

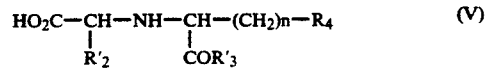

in which $R'_2$, $R'_3$, $R_4$ and n have the same meanings as above,
which is then coupled with a compound of formula (VI) according to the peptide coupling technique described by W. KONIG and R. GEIGER (Ber. 103, 788, 1970):

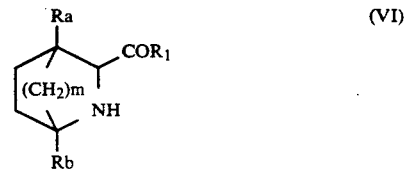

in which Ra, Rb, m and $R_1$ have the same meanings as in the formula (I),
to lead to a compound of formula (I/a), a special case of the compounds of formula (I):

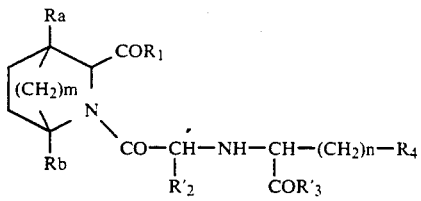
(I/a)

in which Ra, Rb, $R_1$, $R'_2$, $R'_3$, $R_4$, m and n have the same meaning as above,
which, if so desired, when $R'_2$ represents a linear or branched lower alkyl group and $R'_3$ is a linear or branched, lower or higher alkoxy group, may be subjected to the action of a base or an acid to lead to a compound of formula (I/b), a special case of the compounds of formula (I):

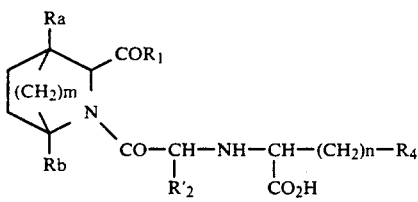
(I/b)

in which Ra, Rb, $R_1$, $R_4$, m and n have the same meaning as in the formula (I), $R'_2$ represents a linear or branched lower alkyl group and $R_3$ represents a hydroxyl group, or alternatively, when $R'_2$ is an alkyl group substituted with a protected amino group and $R'_3$ a linear or branched, lower or higher alkoxy group, subjected to a hydrogenation in the presence of a catalyst such as palladinized charcoal, to lead to a compound of formula (I/c), a special case of the compounds of formula (I):

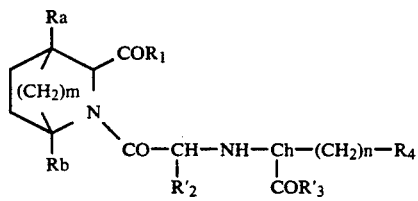
(I/c)

in which Ra, Rb, $R_1$, $R_4$, n and m have the same meanings as in the formula (I), $R'_2$ represents an alkyl group substituted with an amino group and $R'_3$ represents a linear or branched, lower or higher alkoxy group,
which compound (I/c), if so desired, may be subjected to the action of a base, to lead to a compound of formula (I/d), a special case of the compounds of formula (I):

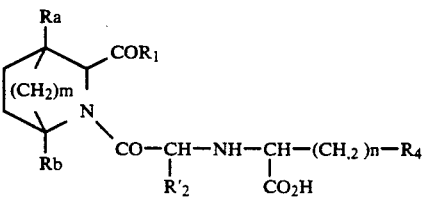
(I/d)

in which Ra, Rb, $R_1$, $R_4$, n and m have the same meanings as in the formula (I), $R'_2$ represents an alkyl group substituted with an amino group and $R_3$ represents a hydroxyl group,
which compounds of formulae (I/a), (I/b), (I/c) and (I/d) are purified by a conventional purification technique, the isomers of which compounds are optionally separated by a conventional separation technique and which are converted, if so desired, to their addition salts with a pharmaceutically acceptable acid or base.

The compounds of formula (VI) in which $R_1$ represents a higher alkoxy group are new and form part of the invention in the same way as the compounds of formula (I), for which they constitute synthesis intermediates.

The compounds of formula (I) possess very advantageous pharmacological properties.

They are endowed, on the one hand, with inhibitory effects of angiotensin I converting enzyme, and on the other hand with antagonist effects of scopolamine-induced amnesia. Through their first property, they can hence counteract arterial hypertensive disease and its consequences, especially at cerebral level, and can create to patients a feeling of well-being, as has been described previously for the first known ACE inhibitor, captopril.

Through the second property, they improve learning and recall performance, the dysfunction of which has been amply observed during aging and, still more, during presenile, senile and vascular degenerative dementia.

This facilitation is observed to a remarkable extent during experimental amnesia induced by a cholinergic antagonist.

The memory enhancing of the compounds of the present invention hence relate especially to cholinergic neurotransmission, the close involvement of which in memory processes is classically demonstrated.

These collective properties hence endow the present compounds with cardiovascular and cerebral protective properties, and with facilitatory properties with respect to the memory functions which are always the outcome of the capacities for attention, vigilance, well-being and memorization.

The memory effects of these compounds are exerted much more intensely than those of the most recent nootropic compound which has been taken as a reference: oxiracetam.

These compounds hence prove useful for the therapeutic, preventive or curative treatment of neurobehavioral disorders associated with stroke, aging and senile or presenile dementia such as Alzheimer's disease, Pick's disease, multi-infarct dementia and Binswanger's disease.

The subject of the present invention is also pharmaceutical compositions containing as active principle at least one compound of general formula (I) or one of its addition salts with a pharmaceutically acceptable acid or base, alone or in combination with one or more non-toxic, inert vehicles or excipients.

Among the pharmaceutical compositions according to the invention, those which are suitable for oral, parenteral or nasal administration, simple or sugar-coated tablets, sublingual tablets, sachets, packets, hard gelatin capsules, sublingual preparations, bars, suppositories, creams, ointments, skin gels, and the like, may be mentioned more especially.

The appropriate dosage varies according to the patient's age and weight, the nature and severity of the condition and also the administration route. The latter may be oral, nasal, rectal or parenteral. Generally speaking, the unit dosage ranges between 0.1 and 100 mg for a treatment administered in 1 to 3 doses per 24 hours.

The examples which follow illustrate the invention and in no way limit the latter.

EXAMPLE 1:
(3S)-2-{(S)-2-[(S)-1-(ETHOXYCARBONYL)-BUTYLAMINO]PROPIONYL}-3-CARBAMOYL-2-AZABICYCLO[2.2.2]OCTANE

Using the (DCC/HOBT) peptide coupling method described by W. KONIG and R. GEIGER (Ber, 103, 788, 1970) the expected product is prepared from 0.02 mol of (3S)-3-carbamoyl-2-azabicyclo[2.2.2]octane, described in Patent FR 2,585,709, and 0.02 mol of (S)-N-[(S)-1-(ethoxycarbonyl)butyl]alanine, described by VINCENT et al (Tetrahedron Letters 23, (1982), 1677–1680), the product being purified by chromatography on silica gel (elution solvent: dichloromethane/ethanol, 90:10) and then lyophilized.

Yield: 58%

Elemental microanalysis:

|  | C % | H % | N % |
|---|---|---|---|
| calculated: | 61.17 | 8.84 | 11.89 |
| found: | 61.01 | 9.04 | 11.93 |

Proton nuclear magnetic resonance (CDCl$_3$):

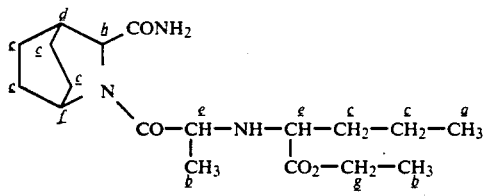

$\underline{a}$ δ = 0.9 ppm (3H,m)
$\underline{b}$ δ = 1.3 ppm (6H,m)
$\underline{c}$ δ = 1.6 ppm (12H,m)
$\underline{d}$ δ = 2.0 ppm (1H,m)
$\underline{e}$ δ between 3.1 and 3.6 ppm (2H,m)
$\underline{f}$ δ = 4.0 ppm (1H,m)
$\underline{g}$ δ = 4.2 ppm (2H,q)
$\underline{h}$ δ = 4.4 ppm (1H,m)

EXAMPLE 2:
(3S)-2-{(S)-2-[(S)-1-CARBOXYBUTYLAMINO]-PROPIONYL}-3-CARBAMOYL-2-AZABICYCLO-[2.2.2]OCTANE 4.25 mmol (1.5 g) of the compound obtained in Example 1 are dissolved in 50 cm$^3$ of 0.1N sodium hydroxide. The solution is left for 24 hours at room temperature, neutralized by adding 1N hydrochloric acid and then evaporated to dryness. The residue is taken up with 50 cm$^3$ of isopropanol, filtered and evaporated, then taken up in 40 cm$^3$ of water. The expected product is obtained after lyophilization.

Yield: 94%

Proton nuclear magnetic resonance (DMSO-d$_6$):

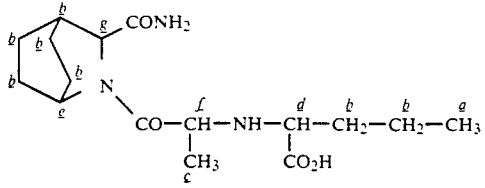

$\underline{a}$ δ = 0.9 ppm (3H,t)
$\underline{b}$ δ = between 1.0 and 2.4 ppm (13H,m)
$\underline{c}$ δ = 1.2 ppm (3H,d)
$\underline{d}$ δ = 3.05 ppm (1H,t)
$\underline{e}$ δ = 3.85 ppm (1H,m)
$\underline{f}$ δ = 3.9 ppm (1H,q)
$\underline{g}$ δ = 4.1 ppm (1H,d)

EXAMPLE 3:
(3S)-2-{(S)-2-[(S)-1-CARBAMOYLBUTYL-AMINO]PROPIONYL}-3-CARBAMOYL-2-AZABICYCLO[2.2.2]OCTANE

Stage A: (S)-N-[(S)-1-Carbamoylbutyl]Alanine 10 g of (S)-N-[(S)-1-(ethoxycarbonyl)butyl]alanine are placed in 100 ml of 28% strength aqueous ammonia solution at 100° C. for 18 hours. After evaporation of the solvent, the residue is taken up with 50 ml of water. The solution is evaporated to dryness, then taken up with 100 ml of isopropanol and evaporated. The expected product is obtained after drying under vacuum.

Yield: 95%

Proton nuclear magnetic resonance (DMSO-d$_6$):

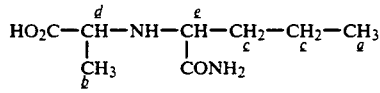

$\underline{a}$ δ = 0.9 ppm (3H,t)
$\underline{b}$ δ = 1.3 ppm (3H,d)
$\underline{c}$ δ between 1.2 and 1.7 ppm (4H,m)
$\underline{d}$ δ = 3.1 ppm (1H,q)
$\underline{e}$ δ = 3.2 ppm (1H,m)

Stage B:
(3S)-2-{(S)-2-[(S)-1-CARBAMOYLBUTYL-AMINO]PROPIONYL}-3-CARBAMOYL-2-AZABICYCLO[2.2.2]OCTANE Using the procedure described in Example 1, but replacing (S)-N-[(S)-1-(ethoxycarbonyl)butyl]alanine by (S)-N-[(S)-1-carbamoylbutyl]alanine obtained in stage A, the expected product is obtained, the product being purified by chromatography on silica gel (elution solvent: dichloromethane/methanol/ammonia solution, 90:10:0.5).

Yield: 22%

Elemental microanalysis:

|  | C % | H % | N % |
|---|---|---|---|
| calculated: | 59.24 | 8.70 | 17.27 |
| found: | 59.38 | 8.78 | 17.35 |

Proton nuclear magnetic resonance spectrum (DMSO-d$_6$):

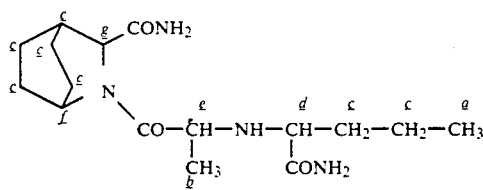

a δ = 0.8 ppm (3H,t)
b δ = 1.1 ppm (3H,d)
c δ between 1.2 and 2.3 ppm (13H,m)
d δ = 2.7 ppm (1H,m)
e δ = 3.4 ppm (1H,m)
f δ = 3.8 ppm (1H,m)
g δ = 4.1 ppm (1H,m)

EXAMPLE 4:
(3S)-2-{(S)-2-[(S)-1-CARBAMOYLBUTYLAMINO]-PROPIONYL}-2-AZABICYCLO[2.2.2]-OCTANE-3-CARBOXYLIC ACID n-OCTYL ESTER

Stage A:
(3S)-2-Azabicyclo[2.2.2]OCTANE-3-Carboxylic Acid n-Octyl Ester Hydrochloride 9.6 ml of thionyl chloride are added dropwise into a 250 ml round-bottomed flask containing 60 ml of n-octanol cooled to 0° C. After stirring for 10 min at 0° C., 18.6 g of (3S)-2-azabicyclo[2.2.2]octane-3-carboxylic acid (described in Patent FR 2,585,709) are added slowly. The reaction mixture is left stirring overnight at room temperature, then heated for 6 hours at 80° C. and again left overnight at room temperature. After adding 100 ml of anhydrous ether and filtering off the unreacted hydrochloride, the filtrate is condensed and then taken up with a water/ether mixture (50:50). The expected product is obtained after concentration of the aqueous phase and then drying under vacuum.

Yield: 81%
Elemental microanalysis:

|  | C % | H % | N % | Cl |
|---|---|---|---|---|
| calculated: | 63.24 | 9.95 | 4.61 | 11.67 |
| found: | 62.90 | 9.93 | 4.65 | 11.33 |

Stage B:
(3S)-2-{(S)-2-[(S)-1-CARBAMOYLBUTYLAMINO]-PROPIONYL}-2-AZABICYCLO[2.2.2]OCTANE-3-CARBOXYLIC ACID n-OCTYL ESTER Using the procedure described in Example 1, but replacing (S)-N-(S)-1-(ethoxycarbonyl)butyl]alanine by (S)-N-[(S)-1-carbamoylbutyl]alanine described in stage A of Example 3, and (3S)-3-carbamoyl-2-azobicyclo[2.2.2]-octane by (3S)-2-azabicyclo[2.2.2]octane-3-carboxylic acid n-octyl ester hydrochloride obtained in stage A (neutralized beforehand with triethylamine), the expected product is obtained from the product being purified by chromatography on silica gel (elution solvent: dichloromethane/ethanol, 95:5).

Yield: 21%
Proton nuclear magnetic resonance (CDCl$_3$):

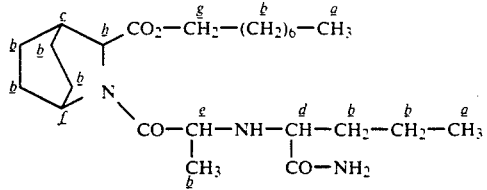

a δ = 0.9 ppm (6H,m)
b δ between 1.15 and 1.90 ppm (27H,m)
c δ = 2.05 ppm (1H,m)
d δ = 2.85 ppm (1H,t)
e δ = 3.4 ppm (1H,q)
f δ = 3.8 ppm (1H,m)
g δ between 4.00 and 4.25 ppm (2H,m)
h δ = 4.4 ppm (1H,m)

EXAMPLE 5:
(3S)-2-{(S)-2-[(S)-1-(ETHOXYCARBONYL)3-PHENYLPROPYLAMINO]PROPIONYL}-3-CARBAMOYL-2-AZABICYCLO[2.2.2]OCTANE

Using the procedure described in Example 1, but replacing (S)-N-[(S)-1-(ethoxycarbonyl)butyl]alanine by (S)-N-[1-(ethoxycarbonyl)-3-phenylpropyl]alanine, described by J. S. Kaltenbronn et al. (Organic Preparations Procedures Int. 15 (1-2), 35–40 (1983)), the expected product is obtained, the product being purified after dissolution in 0.5N hydrochloric acid, filtration to separate the insoluble matter, neutralization of the filtrate, then filtration to separate the precipitate and washing with water.

Yield: 85%
Proton nuclear magnetic resonance (DMSO-d$_6$):

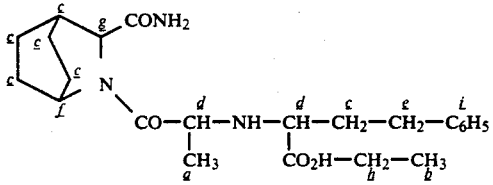

a δ = 1.1 ppm (3H,d)
b δ = 1.2 ppm (3H,t)
c δ between 1.3 and 2.3 ppm (11H,m)
d δ = 2.6 ppm (2H,m)
e δ = 3.2 ppm (2H,m)
f δ = 3.5 ppm (1H,m)
g δ = 4.0 ppm (1H,m)
h δ = 4.1 ppm (2H,q)
i δ = 7.2 ppm (5H,m)

EXAMPLE 6:
(3S)-2-{(S)-2-[(S)-1-CARBOXY-3-PHENYLPROPYLAMINO]PROPIONYL}-3-CARBAMOYL-2-AZABICYCLO[2.2.2]OCTANE 1 g of the compound obtained in Example 5 is dissolved in 50 cm$^3$ of 6N hydrochloric acid and then brought to reflux for 8 hours. After evaporation, the residue is dissolved in 50 cm$^3$ of water and then bound to DOWEX 50 WX8 resin. After washing with water, the product is eluted with a water-pyridine mixture (90:10). The expected product is obtained after evaporation, purified by chromatography on silica gel (elution solvent: acetone/water, 90:10), taken up with water and then lyophilized.

Yield: 13%
Proton nuclear magnetic resonance (DMSO-d$_6$):

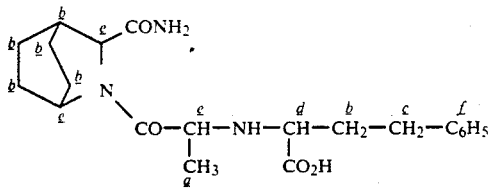

a δ = 1.3 ppm (3H,d)
b δ between 1.2 and 2.2 ppm (11H,m)
c δ = 2.6 ppm (2H,m)
d δ = 3.1 ppm (1H,t)
e δ = 4.0 ppm (3H,m)
f δ = 7.2 ppm (5H,m)

EXAMPLE 7:
(3S)-2-{(S)-2-[(S)-1-(ETHOXYCARBONYL)3-PHENYLPROPYLAMINO]-6-AMINOHEXANOYL}-3-CARBAMOYL-2-AZABICYCLO[2.2.2] OCTANE

Stage A:
(3S)-2-{(S)-2-[(S)-1-(ETHOXYCARBONYL)3-PHENYLPROPYLAMINO]-6-(BENZYLOXYCARBONYLAMINO)HEXANOYL}-3-CARBAMOYL-2-AZABICYCLO-[2.2.2]OCTANE Using the procedure described in Example 1, but replacing (S)-N-[(S)-1-(ethoxycarbonyl)butyl]alanine by (S)-2-[(S)-1-(ethoxycarbonyl)-3-phenylpropylamino]-6-(benzyloxycarbonylamino)hexanoic acid, described in Patent FR 2,619,813, the expected product is obtained.
Yield: 63%
Elemental microanalysis:

|  | C % | H % | N % |
|---|---|---|---|
| calculated: | 67.30 | 7.64 | 9.23 |
| found: | 67.07 | 7.64 | 9.26 |

Stage B:
(3S)-2-{(S)-2-[(S)-1-(ETHOXYCARBONYL)3-PHENYLPROPYLAMINO]-6-AMINOHEXANOYL}-3-CARBAMOYL-2-AZABICYCLO[2.2.2] OCTANE 6.4 g of the product obtained in stage A are dissolved in 60 ml of anhydrous ethanol. After the addition of 0.5 g of palladinized charcoal (10% Pd) and hydrogenolysis at room temperature for 20 hours under a hydrogen pressure of 3 kg/cm$^2$, the mixture is filtered and evaporated. The residue is taken up with 100 ml of water. The solution is filtered and the expected product is obtained after lyophilization.
Yield: 82%
Proton nuclear magnetic resonance (CDCl$_3$):

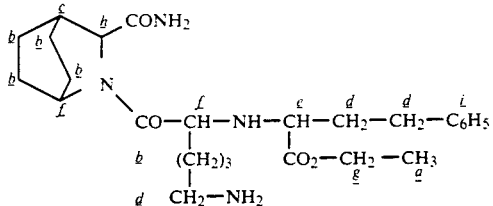

a δ = 1.3 ppm (3H,t)
b δ = 1.7 ppm (14H,m)
c δ = 2.2 ppm (1H,m)
d δ = 2.7 ppm (6H,t)
e δ = 3.1 ppm (1H,m)
f δ between 3.5 and 4.1 ppm (2H,m)
g δ = 4.2 ppm (2H,q)
h δ = 4.4 ppm (1H,m)
i δ = 7.3 ppm (5H,m)

EXAMPLE 8:
(3S)-2-{(S)-2-[(S)-1-CARBOXY-3-PHENYLPROPYLAMINO]-6-AMINOHEXANOYL}-3-CARBAMOYL-2-AZABICYCLO[2.2.2]OCTANE

Using the procedure described in Example 2, but replacing the compound obtained in Example 1 by (3S)-2-{(S)-2-[(S)-1-(ethoxycarbonyl)-3-phenylpropylamino]-6-aminohexanoyl}-3-carbamoyl-2-azabicyclo[2.2.2]octane obtained in Example 7, the expected product is obtained.
Yield: 72%
Proton nuclear magnetic resonance (DMSO-d$_6$):

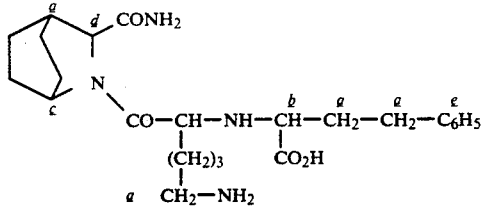

a δ between 2.1 and 3.0 ppm (7H,m)
b δ = 3.4 ppm (1H,m)
c δ = 3.8 ppm (1H,m)
d δ = 4.05 ppm (1H,m)
e δ = 7.1 ppm (5H,m)

EXAMPLE 9:
(3S)-2-{(S)-2-[(S)-1-CARBAMOYL-3-PHENYLPROPYLAMINO]PROPIONYL}-3-CARBAMOYL-2-AZABICYCLO[2.2.2]OCTANE

Stage A:
(S)-N-[(S)-1-CARBAMOYL-3-PHENYLPROPYL]-ALANINE

Using the procedure described in stage A of Example 3, but replacing (S)-N-[(S)-1-(ethoxycarbonyl)-butyl]alanine by (S)-N-[(S)-1-(ethoxycarbonyl)-3-phenylpropyl]alanine, the expected product is obtained.
Yield: 96%
Proton nuclear magnetic resonance (DMSO-d$_6$):

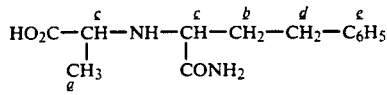

-continued a δ = 1.25 ppm (3H,d)
b δ between 1.7 and 2.0 ppm (2H,m)
c δ between 3.0 and 3.35 ppm (2H,m)
d δ = 2.6 ppm (2H,m)
e δ = 7.3 ppm (5H,m)

Stage B:
(3S)-2-{(S)-2-[(S)-1-CARBAMOYL-3-PHENYL-PROPYLAMINO]PROPIONYL}-3-CARBAMOYL-2-AZABICYCLO[2.2.2]OCTANE Using the procedure described in stage B of Example 3, but replacing (S)-N-[(S)-1-carbamoylbutyl]alanine (S)-N-[(S)-1-carbamoyl-3-phenylpropyl]alanine obtained in the preceding stage, the expected product is obtained after purification on silica gel (elution solvent: dichloromethane/methanol/ammonia solution, 90:10:0.5).

Yield: 24%

Proton nuclear magnetic resonance (DMSO-$d_6$):

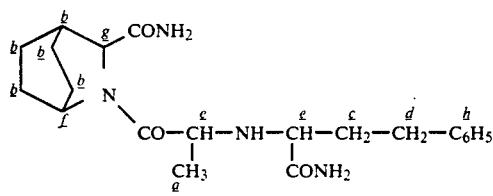

a δ = 1.15 ppm (3H,d)
b δ between 1.20 and 1.90 ppm (9H,m)
c δ = 1.9 ppm (2H,m)
d δ = 2.65 ppm (2H,m)
e δ = 2.80 ppm (2H,m)
f δ = 3.45 ppm (1H,m)
g δ = 4.15 ppm (1H,m)
h δ = 7.2 ppm (5H,m)

EXAMPLE 10:
(3S)-2-{(S)-2-[(S)-1-CARBAMOYL-3-PHENYL-PROPYLAMINO]-6-AMINOHEXANOYL}-2-AZABICYCLO[2.2.2]OCTANE-3-CARBOXYLIC ACID n-OCTYL ESTER DIHYDROCHLORIDE

Stage A:
(S)-2-[(S)-1-CARBAMOYL-3-PHENYL-PROPYLAMINO]-6-(BENZYLOXYCAR-BONYLAMINO)HEXANOIC ACID Using the procedure described in stage A of Example 3, but replacing (S)-N-[(S)-1-(ethoxycarbonyl)-butyl]alanine by (S)-2-[(S)-1-(ethoxycarbonyl)-3-phenyl-propylamino]-6-(benzyloxycarbonylamino)hexanoic acid, the expected product is obtained.

Yield: 85%

Proton nuclear magnetic resonance (DMSO-$d_6$):

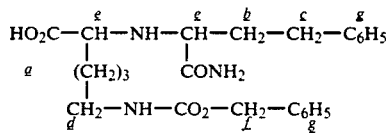

a δ between 0.7 and 1.8 ppm (6H,m)
b δ = 1.9 ppm (2H,m)
c δ = 2.65 ppm (2H,m)
d δ = 3.0 ppm (2H,m)
e δ between 3.15 and 3.5 ppm (2H,m)
f δ = 5.00 ppm (2H,s)
g δ = 7.25 ppm (10H,m)

Stage B:
(3S)-2-{(S)-2-[(S)-1-CARBAMOYL-3-PHENYL-PROPYLAMINO]-6-(BENZYLOXYCAR-BONYLAMINO)-HEXANOYL}-2-AZABICY-CLO[2.2.2]OCTANE-3-CARBOXYLIC ACID n-OCTYL ESTER Using the procedure described in stage B of Example 4, but replacing (S)-N-[(S)-1-carbamoylbutyl]-alanine by (S)-2-[(S)-1-carbamoyl-3-phenylpropylamino]-6-(benzyloxycarbonylamino)hexanoic acid prepared in stage A, the expected product is obtained, the product being purified by chromatography on silica gel (elution solvent: dichloromethane/ethanol, 97:3).

Yield: 26%

Stage C:
(3S)-2-{(S)-2-[(S)-1-CARBAMOYL-3-PHENYL-PROPYLAMINO]-6-AMINOHEXANOYL}-2-AZABICYCLO[2.2.2]OCTANE-3-CARBOXYLIC ACID n-OCTYL ESTER DIHYDROCHLORIDE Using the procedure described in stage B of Example 7, but replacing the product obtained in stage A of Example 7 by the product described in stage B, the expected product is obtained after dissolution of the oily residue in ether, acidification with ethereal hydrogen chloride, filtration, washing with hexane, dissolution in water and lyophilization.

Yield: 61%

Elemental microanalysis:

|  | C % | H % | N % | Cl % |
|---|---|---|---|---|
| calculated: | 61.04 | 8.64 | 8.90 | 11.26 |
| found: | 60.66 | 8.54 | 8.75 | 11.16 |

Proton nuclear magnetic resonance ($D_2O$):

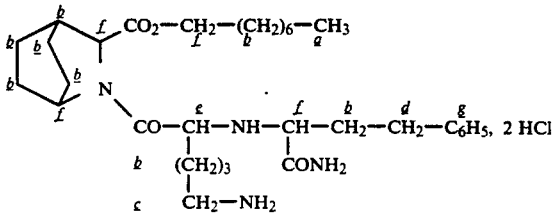

a δ = 0.8 ppm (3H,t)
b δ between 1.0 and 2.1 ppm (29H,m)
c δ = 2.6 ppm (2H,t)
d δ = 2.9 ppm (2H,t)
e δ = 3.6 ppm (1H,t)
f δ about 4.1 ppm (5H,m)
g δ = 7.1 ppm (5H,m)

EXAMPLE 11:
2-{(S)-2-[(S)-1-(ETHOXYCARBONYL)-3-PHENYL-PROPYLAMINO]PROPIONYL}-3-CARBAMOYL-2-AZABICYCLO[2.2.1]HEPTANE, α-ISOMER

Using the procedure described in Example 5, but replacing (3S)-3-carbamoyl-2-azabicyclo[2.2.2]octane by 3-carbamoyl-2-azabicyclo[2.2.1]heptane, α-isomer, described in French Patent No. 89/08,672, the expected product is obtained after chromatography on silica gel (elution solvent: dichloromethane/methanol/ammonia solution, 95:5:0.5).

Yield: 19%

Elemental microanalysis:

|  | C % | H % | N % |
| --- | --- | --- | --- |
| calculated: | 65.81 | 7.78 | 10.47 |
| found: | 65.06 | 7.94 | 10.18 |

Proton nuclear magnetic resonance (DMSO-$d_6$):

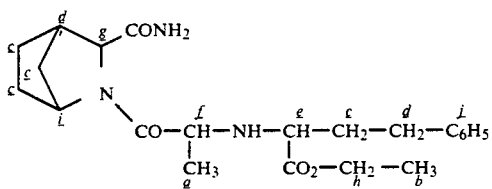

$\underline{a}\,\delta = 1.1$ ppm (3H,d)
$\underline{b}\,\delta = 1.2$ ppm (3H,t)
$\underline{c}\,\delta$ between 1.3 and 1.9 ppm (8H,m)
$\underline{d}\,\delta = 2.6$ ppm (3H,m)
$\underline{e}\,\delta = 3.1$ ppm (1H,m)
$\underline{f}\,\delta = 3.6$ ppm (1H,m)
$\underline{g}\,\delta = 4.0$ ppm (1H,m)
$\underline{h}\,\delta = 4.1$ ppm (2H,q)
$\underline{i}\,\delta = 4.4$ ppm (1H,m)
$\underline{j}\,\delta = 7.2$ ppm (5H,m)

EXAMPLE 12:
2-{(S)-2-[(S)-1-(ETHOXYCARBONYL)-BUTYLAMINO]PROPIONYL}-3-CARBAMOYL-2-AZABICYCLO[2.2.1]HEPTANE, α-ISOMER

Using the procedure described in Example 1, replacing (3S)-3-carbamoyl-2-azabicyclo[2.2.2]octane by 3-carbamoyl-2-azabicyclo[2.2.1]heptane, α-isomer, described in French Patent No. 89/08,672, the expected product is obtained.

Yield: 38%

Elemental microanalysis:

|  | C % | H % | N % |
| --- | --- | --- | --- |
| calculated: | 60.16 | 8.61 | 12.38 |
| found: | 60.30 | 8.64 | 12.16 |

Proton nuclear magnetic resonance (DMSO-$d_6$):

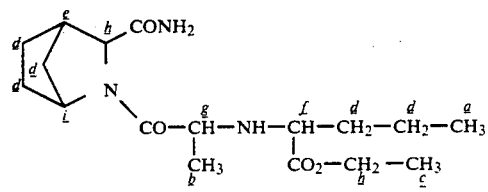

$\underline{a}\,\delta = 0.8$ ppm (3H,t)
$\underline{b}\,\delta = 1.1$ ppm (3H,d)
$\underline{c}\,\delta = 1.2$ ppm (3H,t)
$\underline{d}\,\delta =$ between 1.0 and 1.7 ppm (10H,m)
$\underline{e}\,\delta = 2.6$ ppm (1H,m)
$\underline{f}\,\delta = 3.1$ ppm (1H,t)
$\underline{g}\,\delta = 3.5$ ppm (1H,q)
$\underline{h}\,\delta = 4.1$ ppm (3H,m)
$\underline{i}\,\delta = 4.4$ ppm (1H,m)

EXAMPLE 13:
(3S)-2-{(S)-2-[(S)-1-(ETHOXYCARBONYL)-BUTYLAMINO]PROPIONYL}-3-CARBAMOYL-1,4-DIMETHYL-2-AZABICYCLO[2.2.2]OCTANE

Using the procedure described in Example 1, but replacing (S)-carbamoyl-2-azabicyclo[2.2.2]octane by (S)-carbamoyl-1,4-dimethyl-2-azabicyclo[2.2.2]octane, described in French Patent No. 89/08,672, the expected product is obtained.

EXAMPLE 14:
(3S)-2-{(S)-1-CARBAMOYLBUTYLAMINO]PROPIONYL}-4-METHYL-1-ISOPROPYL-2-AZABICYCLO[2.2.2]OCTANE-3-CARBOXYLIC ACID n-OCTYL ESTER

Using the procedure described in Example 4, but replacing (3S)-2-azabicyclo[2.2.2]octane-3-carboxylic acid in stage A by (3S)-4-methyl-1-isopropyl-2-azabicyclo[2.2.2]octane-3-carboxylic acid, described in French Patent No. 89/08,672, the expected product is obtained.

PHARMACOLOGICAL STUDY OF THE DERIVATIVES OF THE INVENTION

EXAMPLE 15: Inhibitory Effects on Angiotensin I Converting Enzyme

The activity of the converting enzyme is determined in vitro according to the method of RYAN J. W. et al. (Biochem. J., 1977, 167, 501–504), which utilizes the reaction of conversion of hippurylhistidylleucine (HHL) to hippuric acid. The latter is assayed by liquid scintillation after extraction with ethyl acetate. The inhibitory effect of a compound is determined by incubation at different doses in the presence of the substrate and the converting enzyme. The results are expressed as the $IC_{50}$ of these compounds. Under these conditions, the compound of Example 2 possesses an $IC_{50}$ equal to $5 \times 10^{-8}$M, that of the compound of Example 8 being $1.8 \times 10^{-8}$M.

EXAMPLE 16: Promnesic Effects

Male OFA rats (Iffa-Credo) weighting 210–240 g are placed in individual cages under standard environmental conditions. The memory test is a test of one trial-passive avoidance in which experimental amnesia is induced by prior injection of scopolamine.

The apparatus consists of a two-compartment enclosure separated by an automatically closing door.

On the day of conditioning, each animal is placed during 60 seconds in the aversive compartment (white, brightly lit).

Then the door is rapidly open and the rat can freely enter the compartment where it feels secure (black and dark). Transit thereto triggers closing of the door, followed by application to the animal of an unescapable electric shock via the floor of the dark compartment (0.6 mA; 3 seconds).

Memory retention is measured 24 hours later under the same conditions. For this purpose, the latency of transit to the black compartment is measured and the maximum observation time is set at 300 seconds.

Under these conditions, the control animals do not return to the punished black compartment. In the amnesic scopolamine-treated animals (1 mg/kg I.P. 30 minutes before initial conditioning) the latency of transit is greatly decreased relative to the control animals.

The memory enhancing effect of the compounds under investigation is measured in animals receiving scopolamine. These compounds are administered I.P. twice daily during the 3 days preceding the memory test, and then 1 hour before the conditioning test (i.e. 30 minutes before the scopolamine).

The promnesic effects of the compounds increase the transit time relative to the amnesic animals.

The compounds of the present invention are compared to oxiracetam, the nootropic agent most recently proposed in the therapy of memory disorders.

Results:

In the non-amnesic control animals, the mean latency time of retention is 295 seconds and 95% of the animals never return to the punished compartment.

In the amnesic control animals, the mean latency time of retention is very significantly decreased (111.9 seconds; p<0.001), and only 11% of the animals do not return to the punished compartment (p<0.005).

The compounds of the present invention very significantly counteract the scopolamine-induced amnesia. This protective effect is observed in the case of some of the compounds at doses of 0.01 mg/kg and above, and the range of promnesic doses is then from 0.01 to 1 mg/kg. This effect follows an inverted U-shaped curve characteristic of compounds facilitating memory performance.

The following table collates, as an example, the results obtained with two of the compounds of the present invention and those obtained with the most recent nootropic compound: oxiracetam. Under our conditions, oxiracetam exerts a protective activity only at 30 mg/kg and above.

|  | Dose in mg/kg | | | | | | | |
|---|---|---|---|---|---|---|---|---|
|  | 0 | 0.003 | 0.01 | 0.03 | 0.1 | 0.3 | 1 | 3 |
| Example 3 | | | | | | | | |
| Latency of transit (s) | 111.9 | 108.2 | 119.3 | 166.4* | 171.6* | 182.6** | 125.2 | 121.3 |
| % Retention at 300 sec. | 11% | 5% | 10% | 35%** | 45%*** | 40%*** | 20% | 10% |
| Example 4 | | | | | | | | |
| Latency of transit (s) | 111.9 | 115.6 | 149.3* | 205.1*** | 207.2*** | 202.1*** | 171.5** | 106.7 |
| % Retention at 300 sec. | 11% | 10% | 30% | 50%** | 55%*** | 40%** | 40%* | 5% |

|  | Dose in mg/Kg. | | | | | | | |
|---|---|---|---|---|---|---|---|---|
|  | 0 | 1 | 3 | 10 | 30 | 100 | 300 | 1000 |
| OXIRACETAM | | | | | | | | |
| Latency in transit (s) | 111.9 | 97.4 | 126.5 | 115.3 | 150.1* | 182.5* | 200.2*** | 175.8* |
| % Retention at 300 sec. | 11% | 10% | 10% | 5% | 30%* | 40%** | 45%** | 30% |

*p < 0.05
**p < 0.01
***p < 0.005
vs scopolamine controls
Latency of transit: Mann-Whitney test
% retension 300 sec: Log-rank test on the evolution of percent of avoidance during the 300 seconds of the retention test Thus, the nootropic effect of the compounds of the present invention is exerted, in particular, via cholinergic neurotransmission, which they facilitate so as to improve the capacities for memorization and recall.

EXAMPLE 17: Pharmaceutical Composition

Tablet: preparation formula for 1000 tablets containing a 2 mg dose of active principle.

| | |
|---|---|
| (3S)-2-{(S)-2-[(S)-1-(Ethoxycarbonyl)butyl-amino]propionyl}-3-carbamoyl-2-azabicyclo-[2.2.2]octane | 2 g |
| Hydroxypropylcellulose | 2 g |
| Wheat starch | 10 g |
| Lactose | 100 g |
| Magnesium stearate | 3 g |
| Talc | 3 g |

We claim:

1. A compound selected from those of formula (I):

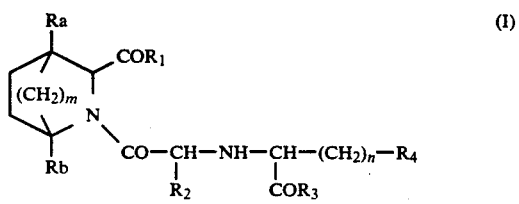

in which:

$R_1$ represents linear or branched, lower or higher alkoxy, or amino unsubstituted or substituted with one or two linear or branched lower alkyl groups, $R_2$ represents linear or branched lower alkyl unsubstituted or substituted with amino, $R_3$ represents an amino group, a linear or branched, lower or higher alkoxy, or hydroxyl, with the proviso, however, that at least one amino group is present in $R_1$ or $R_3$, $R_4$ represents hydrogen or phenyl, m is equal to 1 or 2, n is between 1 and 6, and Ra and Rb, which may be identical or different, represent a hydrogen atom when m=1, or linear or branched lower alkyl or hydrogen when m=2, the term lower indicating that the group so described comprise from 1 to 6 carbon atoms the term higher indicating that the group so described comprises 7 to 12 carbon atoms, their enantiomers, diastereoisomers, and epimers, as well as their addition salts with a pharmaceutically-acceptable acid or base.

2. A compound as claimed in claim 1, wherein m is 1.

3. A compound as claimed in claim 1, wherein m is 2.

4. A compound as claimed in claim 1, wherein $R_1$ represents amino.

5. A compound as claimed in claim 1, wherein $R_1$ represents n-octyloxy and $R_3$ represents amino.

6. A pharmaceutical composition containing as active principle an effective amount of at least one compound of claim 1, alone or in combination with one or more pharmaceutically-acceptable vehicles or excipients.

7. A method for treating an animal or human living body afflicted with a disease resulting from arterial hypertension and neurobehavioral disorders associated with aging and with senile or presenile degenerative dementia, comprising the step of administering to the said living body an amount of a compound of claim 1 which is suitable for alleviation of said condition.

* * * * *

UNITED STATES PATENT AND TRADEMARK OFFICE
CERTIFICATE OF CORRECTION

PATENT NO. : 5,151,432

DATED : Sep. 29, 1992

INVENTOR(S) : Michel Vincent, Georges Remond, Bernard Portevin, Yolande Herve, Jean Lepagnol It is certified that error appears in the above-identified patent and that said Letters Patent is hereby corrected as shown below:

Column 8, approximately line 43; "$CO_2H-CH_2-CH_3$" should read -- $CO_2-CH_2-CH_3$ --.

Column 14, approximately line 6; "betweem" should read --between--.

Column 14, line 24; "(3S)-2-{(S)-1-" should read -- (3S)-2-{(S)-2-[(S)-1- --.

Column 16, line 67; "represents an amino group, a linear" should read -- represents amino, linear --. (Cl. 1, ln. 11-PA 12-19-90, P. 1)

Column 17, line 7; "resent a hydrogen atom when" should read -- resent hydrogen when --. (Cl. 1, PA 12-19-90, 2nd line from bottom)

Column 17, line 10; "comprise from 1" should read --comprises 1--. (PA 12-19-90, pg. 2, 7th ln. down)

Signed and Sealed this

Twelfth Day of October, 1993

Attest:

BRUCE LEHMAN

Attesting Officer

Commissioner of Patents and Trademarks